United States Patent
Fagerstrom et al.

(10) Patent No.: US 7,900,637 B2
(45) Date of Patent: Mar. 8, 2011

(54) DEVICE AND METHOD FOR THE ADMINISTRATION OF A SUBSTANCE

(75) Inventors: Karl-Olov Fagerstrom, Kagerod (SE); Henri Hansson, Helsingborg (SE)

(73) Assignee: Niconovum AB, Helsingborg (SE)

( * ) Notice: Subject to any disclaimer, the term of this patent is extended or adjusted under 35 U.S.C. 154(b) by 478 days.

(21) Appl. No.: 10/481,979

(22) PCT Filed: Jun. 24, 2002

(86) PCT No.: PCT/SE02/01231
§ 371 (c)(1), (2), (4) Date: Dec. 23, 2003

(87) PCT Pub. No.: WO03/000324
PCT Pub. Date: Jan. 3, 2003

(65) Prior Publication Data
US 2004/0159326 A1 Aug. 19, 2004

(30) Foreign Application Priority Data
Jun. 25, 2001 (SE) ..................... 0102276

(51) Int. Cl.
*A24F 47/00* (2006.01)
*B65D 83/14* (2006.01)
(52) U.S. Cl. .................... 131/271; 222/635
(58) Field of Classification Search ........... 131/270
See application file for complete search history.

(56) References Cited

U.S. PATENT DOCUMENTS

| | | | |
|---|---|---|---|
| 865,026 A | | 9/1907 | Ellis |
| 940,521 A | | 11/1909 | Endicott |
| 2,933,259 A | * | 4/1960 | Raskin .................... 239/405 |
| 3,069,314 A | * | 12/1962 | Jenkins .................... 424/40 |
| 3,314,578 A | * | 4/1967 | La Mura .................. 222/402.25 |
| 3,767,125 A | * | 10/1973 | Gehres et al. ............... 239/552 |
| 3,777,029 A | | 12/1973 | Magid |
| 3,877,468 A | | 4/1975 | Lichtneckert et al. |
| 4,317,837 A | | 3/1982 | Kehoe et al. |
| 4,579,858 A | | 4/1986 | Ferno |
| 4,593,572 A | | 6/1986 | Linley, Jr. |
| 4,655,231 A | | 4/1987 | Ray et al. |

(Continued)

FOREIGN PATENT DOCUMENTS

CN 1089834 7/1994

(Continued)

OTHER PUBLICATIONS

Wikipedia, Sublingual, http://en.wikipedia.org/w/index.php?title=Sublingual&oldid=218150641 (viewed on Jun. 16, 2008, 3:35 p.m. ET).*

(Continued)

*Primary Examiner* — Richard Crispino
*Assistant Examiner* — Michael J Felton
(74) *Attorney, Agent, or Firm* — Womble Carlyle Sandridge & Rice, PLLC (57) ABSTRACT

The present invention relates to an aerosol spray device (10, 20, 30, 40) for administration of a substance, specifically a substance having a disagreeable taste, such as nicotine, to the oral cavity of a subject; to an actuator (16, 26, 36, 46) included in said spray device and to methods for delivering the substance.

17 Claims, 2 Drawing Sheets

U.S. PATENT DOCUMENTS

| | | | |
|---|---|---|---|
| 4,674,491 A | 6/1987 | Brugger et al. | |
| 4,696,315 A | 9/1987 | Summers | |
| 4,817,640 A | 4/1989 | Summers | |
| 4,835,162 A | 5/1989 | Abood | |
| 4,885,173 A * | 12/1989 | Stanley et al. | 424/440 |
| 4,907,605 A | 3/1990 | Ray et al. | |
| 4,920,989 A * | 5/1990 | Rose et al. | 131/270 |
| 4,945,929 A | 8/1990 | Egilmex | |
| 4,967,733 A | 11/1990 | Rousseau | |
| 4,971,079 A | 11/1990 | Talapin et al. | |
| 5,069,904 A | 12/1991 | Masterson et al. | |
| 5,077,104 A | 12/1991 | Hunt et al. | |
| 5,135,753 A | 8/1992 | Baker et al. | |
| 5,167,242 A | 12/1992 | Turner | |
| 5,268,209 A | 12/1993 | Hunt et al. | |
| 5,284,163 A | 2/1994 | Knudsen et al. | |
| 5,318,523 A | 6/1994 | Lu | |
| 5,488,962 A | 2/1996 | Perfetti et al. | |
| 5,501,858 A | 3/1996 | Fuisz | |
| 5,507,278 A | 4/1996 | Karell | |
| 5,525,351 A | 6/1996 | Dam et al. | |
| 5,543,424 A | 8/1996 | Carlsson et al. | |
| 5,549,906 A | 8/1996 | Santus et al. | |
| 5,573,774 A | 11/1996 | Keenan | |
| 5,643,905 A | 7/1997 | Moormann et al. | |
| 5,654,003 A | 8/1997 | Fuisz et al. | |
| 5,656,255 A | 8/1997 | Jones et al. | |
| 5,692,493 A | 12/1997 | Weinstein et al. | |
| 5,721,257 A | 2/1998 | Baker et al. | |
| 5,733,574 A | 3/1998 | Dam et al. | |
| 5,810,018 A * | 9/1998 | Monte | 131/270 |
| 5,834,011 A | 11/1998 | Rose et al. | |
| 5,939,100 A | 8/1999 | Albrechtsen et al. | |
| 5,955,098 A | 9/1999 | Dugger, III | |
| 6,024,097 A | 2/2000 | Von Wielligh et al. | |
| 6,102,036 A * | 8/2000 | Slutsky et al. | 128/203.15 |
| 6,110,495 A | 8/2000 | Dam et al. | |
| 6,129,936 A | 10/2000 | Gustafsson et al. | |
| 6,174,496 B1 * | 1/2001 | Stein | 422/5 |
| 6,223,744 B1 * | 5/2001 | Garon | 128/200.14 |
| 6,264,981 B1 | 7/2001 | Zhang et al. | |
| 6,280,761 B1 | 8/2001 | Santus et al. | |
| 6,344,222 B1 | 2/2002 | Cherukuri et al. | |
| 6,358,527 B1 | 3/2002 | Gilis et al. | |
| 6,841,557 B2 | 1/2005 | Anderson et al. | |
| 6,845,777 B2 | 1/2005 | Pera | |
| 6,849,624 B2 | 2/2005 | Ballard et al. | |
| 6,855,820 B2 | 2/2005 | Broom et al. | |
| 6,858,624 B2 | 2/2005 | Hagen et al. | |
| 6,861,434 B2 | 3/2005 | Stack | |
| 6,893,654 B2 | 5/2005 | Pinney et al. | |
| 6,932,971 B2 | 8/2005 | Bachmann et al. | |
| 6,958,143 B2 | 10/2005 | Choi et al. | |
| 6,958,323 B2 | 10/2005 | Olivera et al. | |
| 6,960,574 B2 | 11/2005 | Prokai | |
| 6,982,089 B2 | 1/2006 | Tobinick | |
| 2001/0029959 A1 | 10/2001 | Burgard et al. | |
| 2002/0009523 A1 | 1/2002 | Gustaesson | |
| 2002/0010198 A1 | 1/2002 | Jerussi et al. | |
| 2002/0015687 A1 | 2/2002 | Bellamy et al. | |
| 2003/0077297 A1 | 4/2003 | Chen et al. | |
| 2003/0082109 A1 | 5/2003 | Gorenstein | |
| 2003/0124191 A1 | 7/2003 | Besse et al. | |
| 2003/0180360 A1 | 9/2003 | Am Ende et al. | |
| 2003/0224048 A1 | 12/2003 | Walling | |
| 2004/0013752 A1 | 1/2004 | Wolfson | |
| 2005/0009813 A1 | 1/2005 | Moormann et al. | |
| 2005/0009882 A1 | 1/2005 | Farr | |
| 2005/0013856 A1 | 1/2005 | Trivedi et al. | |
| 2005/0020641 A1 | 1/2005 | Sellers et al. | |
| 2005/0042173 A1 | 2/2005 | Besse et al. | |
| 2005/0058609 A1 | 3/2005 | Nazeri | |
| 2005/0089524 A1 | 4/2005 | Sanderson et al. | |
| 2005/0100513 A1 | 5/2005 | Watkins et al. | |
| 2005/0107397 A1 | 5/2005 | Galambos et al. | |
| 2005/0118272 A1 | 6/2005 | Besse et al. | |
| 2005/0123502 A1 | 6/2005 | Chan et al. | |
| 2005/0136047 A1 | 6/2005 | Ennifar et al. | |
| 2005/0182063 A1 | 8/2005 | Yohannes | |
| 2005/0197343 A1 | 9/2005 | Gmeiner et al. | |
| 2005/0222270 A1 | 10/2005 | Olney et al. | |
| 2005/0227998 A1 | 10/2005 | Voelker | |
| 2005/0261289 A1 | 11/2005 | Flohr et al. | |
| 2005/0277626 A1 | 12/2005 | Dinan et al. | |
| 2005/0282823 A1 | 12/2005 | Breining et al. | |
| 2006/0057207 A1 | 3/2006 | Ziegler et al. | |
| 2006/0058328 A1 | 3/2006 | Bhatti et al. | |
| 2006/0062835 A1 | 3/2006 | Weil | |
| 2006/0084656 A1 | 4/2006 | Ziegler et al. | |
| 2006/0252773 A1 | 11/2006 | Ceci | |
| 2006/0276551 A1 | 12/2006 | Shytle et al. | |

FOREIGN PATENT DOCUMENTS

| | | |
|---|---|---|
| CN | 1511550 | 7/2004 |
| CN | 1557177 | 12/2004 |
| DE | 2313996 | 10/1974 |
| DE | 2526702 | 12/1976 |
| DE | 3241437 | 5/1984 |
| DE | 4301782 | 8/1994 |
| DE | 19639343 | 4/1998 |
| DE | 29800300 | 4/1998 |
| DE | 19943491 | 3/2001 |
| EP | 205133 | 12/1986 |
| EP | 215682 | 3/1987 |
| EP | B0324794 | 7/1989 |
| EP | 377520 | 7/1990 |
| EP | 472428 | 2/1992 |
| EP | 485421 | 5/1992 |
| EP | 500658 | 9/1992 |
| EP | 506774 | 10/1992 |
| EP | 506860 | 10/1992 |
| EP | 0557129 | 8/1993 |
| EP | 570327 | 11/1993 |
| EP | 0619729 | 10/1994 |
| EP | 680326 | 11/1995 |
| EP | 0745380 | 12/1996 |
| EP | 0839544 | 5/1998 |
| EP | 850182 | 7/1998 |
| EP | 0904055 | 3/1999 |
| EP | 0916339 | 5/1999 |
| EP | 1023069 | 8/2000 |
| EP | 1069900 | 1/2001 |
| EP | 1136487 | 9/2001 |
| EP | 1267849 | 1/2003 |
| EP | 1272218 | 1/2003 |
| EP | 1448196 | 8/2004 |
| EP | 1 409 049 B9 | 12/2004 |
| EP | 1509227 | 3/2005 |
| EP | 1534254 | 6/2005 |
| EP | 1539149 | 6/2005 |
| EP | 1539764 | 6/2005 |
| EP | 1539765 | 6/2005 |
| EP | 1551393 | 7/2005 |
| EP | 1589952 | 11/2005 |
| EP | 1624845 | 2/2006 |
| EP | 1624895 | 2/2006 |
| EP | 1634498 | 3/2006 |
| EP | 1737431 | 1/2007 |
| FR | 2147652 | 3/1973 |
| FR | 2467604 | 4/1981 |
| FR | 2608156 | 6/1988 |
| FR | 2688400 | 9/1993 |
| FR | 2698268 | 5/1994 |
| FR | 2788982 | 8/2000 |
| FR | 2792200 | 10/2000 |
| GB | 1528391 | 10/1978 |
| GB | 2030862 | 4/1980 |
| GB | 2125699 | 3/1984 |
| GB | 2255892 | 11/1992 |
| GB | 2289204 | 11/1995 |
| GB | 2308992 | 7/1997 |
| GB | 2393392 | 3/2004 |
| JP | 52114010 | 9/1977 |
| JP | 62228022 | 10/1987 |
| JP | 1243945 | 9/1989 |
| JP | 2072118 | 3/1990 |
| JP | 2005082587 | 3/2005 |

| | | |
|---|---|---|
| JP | 2005103113 | 4/2005 |
| JP | 2005320342 | 11/2005 |
| KP | 2001078976 | 8/2001 |
| RU | 2029474 | 2/1995 |
| SU | 1232260 | 5/1986 |
| SU | 1268141 | 11/1986 |
| WO | WO-8302892 | 9/1983 |
| WO | WO-9101132 | 2/1991 |
| WO | WO-9101656 | 2/1991 |
| WO | WO-9104757 | 4/1991 |
| WO | WO-9106288 | 5/1991 |
| WO | WO-9109599 | 7/1991 |
| WO | WO-9109731 | 7/1991 |
| WO | WO 9312764 | 7/1993 |
| WO | WO-9416708 | 8/1994 |
| WO | WO-9503050 | 2/1995 |
| WO | WO 9520411 | 8/1995 |
| WO | WO-9702273 | 1/1997 |
| WO | WO-9710162 | 3/1997 |
| WO | WO-9742941 | 11/1997 |
| WO | WO-9915171 | 4/1999 |
| WO | WO 9965550 | 12/1999 |
| WO | WO-0019977 | 4/2000 |
| WO | WO-0038686 | 7/2000 |
| WO | WO-0044559 | 8/2000 |
| WO | WO-0045795 | 8/2000 |
| WO | WO-0056281 | 9/2000 |
| WO | WO-0119401 | 3/2001 |
| WO | WO-0130288 | 5/2001 |
| WO | WO-0137814 | 5/2001 |
| WO | WO-02076229 | 10/2002 |
| WO | WO-02102357 | 12/2002 |
| WO | WO-03013719 | 2/2003 |
| WO | WO-03045437 | 6/2003 |
| WO | WO-03053175 | 7/2003 |
| WO | WO-03055486 | 7/2003 |
| WO | WO-03077846 | 9/2003 |
| WO | WO-2004002446 | 1/2004 |
| WO | WO-2004004478 | 1/2004 |
| WO | WO-2004004479 | 1/2004 |
| WO | WO-2004004480 | 1/2004 |
| WO | WO-03061399 | 3/2004 |
| WO | WO-2004032644 | 4/2004 |
| WO | WO-2004056219 | 7/2004 |
| WO | WO-2004056363 | 7/2004 |
| WO | WO-2004064811 | 8/2004 |
| WO | WO-2004068964 | 8/2004 |
| WO | WO-2004068965 | 8/2004 |
| WO | WO-2004103372 | 12/2004 |
| WO | WO-2005007655 | 1/2005 |
| WO | WO-2005018348 | 3/2005 |
| WO | WO-2005023227 | 3/2005 |
| WO | WO-2005023781 | 3/2005 |
| WO | WO-2005028484 | 3/2005 |
| WO | WO-2005034968 | 4/2005 |
| WO | WO-2005040338 | 5/2005 |
| WO | WO-2005053691 | 6/2005 |
| WO | WO-2005066126 | 7/2005 |
| WO | WO-2006000232 | 1/2006 |
| WO | WO-2006008040 | 1/2006 |
| WO | WO-2006008041 | 1/2006 |
| WO | WO-2006028344 | 3/2006 |
| WO | WO-2006029349 | 3/2006 |
| WO | WO-2006037418 | 4/2006 |
| WO | WO-2006041769 | 4/2006 |
| WO | WO-2005084126 | 11/2006 |
| WO | WO-2006115202 | 11/2006 |
| WO | WO-2006119884 | 11/2006 |
| WO | WO-2006138682 | 12/2006 |
| WO | WO-2007006117 | 1/2007 |

OTHER PUBLICATIONS

"Actuator." Merriam-Webster Online Dictionary. 2010. Merriam-Webster Online. May 18, 2010 <http://www.merriam-webster.com/dictionary/actuator>.*

Axelsson et al., "The Anti-smoking Effect of chewing gum with nicotine of high and low bioavailability"; 3rd World Conference on Smoking and Health, New York, 1975.

Mihranyan et al., "Sorption of nicotine to cellulose powders", European Journal Pharmaceutical Sciences; 2004; 279-286; 22(4).

Mihranyan, "Engineering of Native Cellulose Structure for Pharmaceutical Applications, Influence of Cellulose Crystallinity Index, Surface Area and Pore Volume on Sorption Phenomena", ACTA Universitatis Upsaliensis Uppsala; 2005; 1-58.

Molander et al., "Pharmacokinetic investigation of a nicotine sublingual tablet", .Eur. J. Clin. Pharmacol. 2001; 813-9; vol. 56(11).

Morjaria et al., "In Vitro Release of Nicotine From Chewing Gum Formulations", Dissolution Technologies; May 2004; 12-15; vol. 11(2).

* cited by examiner

DEVICE AND METHOD FOR THE ADMINISTRATION OF A SUBSTANCE

TECHNICAL FIELD

The present invention relates to an aerosol spray device for administration of a substance, specifically a substance having a disagreeable taste, such as nicotine, to the oral cavity of a subject; to an actuator included in said spray device and to methods for delivering the substance.

BACKGROUND OF THE INVENTION

Oral administration of a substance, such as a drug or medicament, is frequently used, such as in the form of aerosol sprays for inhalation for the treatment of asthma. Another area of oral administration of a substance, such as a drug or medicament, is the area of nicotine-replacement therapy to give up smoking. Several apparatuses for the administration of nicotine containing aerosols have been described, such as in U.S. Pat. No. 5,810,018, U.S. Pat. No. 4,593,572 and U.S. Pat. No. 4,945,929.

One problem experienced with such medicaments being inhaled or administered locally in the oral cavity is the effects of substances having a disagreeable taste being distributed to the oral cavity of an individual. This is a problem in general with irritating and bad tasting drug substances and specifically a problem with nicotine. Such substances are influencing the taste and irritation sensory sites in the mouth and can cause problems when administered locally in the oral cavity to be absorbed through the oral mucosa. This is a particular problem when the drug is deposited on the back of the tongue where there is a high density of taste buds and in the upper throat where reflexes for nausea can be triggered.

When using traditional equipment for oral administration of an aerosol spray, a large part of the administered dose will end up in the whole oral cavity, the pharynx and/or the bronchial tree of the respiratory tract depending on the droplet size. Medicaments associated with inhalation, such as asthma drugs, are preferentially applied locally in the respiratory tract and lungs for a rapid and efficient effect. Still, not all orally sprayed medicaments are to be delivered to the respiratory tract and lungs, but are given locally in the oral cavity for uptake through the oral mucous membrane.

One such medicament is nicotine. Nicotine is an organic compound that is the principal alkaloid of tobacco. Nicotine is the chief addictive ingredient in the tobacco used in cigarettes, cigars, snuff and the like. Nicotine is also an addictive drug, though, and smokers characteristically display a strong tendency to relapse after having successfully stopped smoking for a time. Nicotine is the worlds second most used drug, after caffeine from coffee and tea.

The main problem with tobacco smoking is its enormous implications on health. Today it is estimated that smoking related diseases cause some 3-4 million deaths per year. This grim consequence of tobacco smoking has urged many medical associations and health authorities to take very strong actions against the use of tobacco.

Tobacco smoking can result in a dependence disorder. The WHO has in its International Classification of Disorders a diagnosis called Tobacco Dependence. Others like the American Psychiatric Association call the addiction Nicotine Dependence. Even though tobacco smoking is decreasing in many developed countries today it is hard to see how the societies could get rid of the worlds second most used drug.

Nicotine containing medications are currently the dominating treatments for tobacco dependence. There is also evidence of broader use of these medications like for smoking reduction and long term maintenance/substitution.

When smoking a cigarette, nicotine is quickly absorbed into the smoker's blood and reaches the brain within eight seconds after inhalation. The poisonous, toxic, carcinogenic, and addictive nature of smoking has provided efforts for methods, compositions and devices, which help in breaking the habit of smoking cigarettes.

For those who are unable to give up smoking there are several ways and forms of nicotine replacement products available on the market; such as nicotine gum. Several methods and means have been described for diminishing the desire of a subject to use tobacco, which comprises the step of administering to the subject nicotine or a derivative thereof as described in e.g. U.S. Pat. No. 5,939,100, U.S. Pat. No. 4,967,773, U.S. Pat. No. 865,026, U.S. Pat. No. 940,521. Aerosol compositions are described in GB 1 528 391, GB 2 030 862, U.S. Pat. No. 5,810,018, EP 0 557 129 and U.S. Pat. No. 4,593,572 and are adapted to be sprayed into the mouth of the user. Also, inhaling devices resembling a cigarette are known for ingestion of nicotine vapours orally as suggested in U.S. Pat. No. 5,167,242. Finally, ways of administrating nicotine is by way of delivering directly into the nasal cavity is known from U.S. Pat. No. 4,579,858, DE 32 41 437 and WO/93 127 64. Said means and methods address the problems associated with addiction to nicotine.

However, as stated above, a major drawback with the presently available nicotine containing aerosol spray devices is the fact that they deliver a large part of the dose in the back of the mouth cavity. This generally results in an experience of a bad and disagreeable taste, nausea and other irritations.

Several proposals have been provided for solving said problem of bad and disagreeable taste. Flavourants, such as tobacco flavouring, menthol or methyl salicylate, for example, may be added to impregnate such nicotine taste to produce an oral nicotine spray with a pharmacologically acceptable flavour. U.S. Pat. No. 4,967,773 describes the addition of liquorice, cocoa, aniseed and peppermint to a nicotine lozenge to avoid the bad taste of nicotine.

Still, none of the above mentioned means and methods addresses the problems associated with the bad taste of nicotine in any other way but addition of different flavouring agents.

Even though flavouring to conceal the bad taste of a medicament may partly circumvent the problem of bad tasting drugs it includes the further step in the production of the medicament of adding the desired flavouring agent. Moreover, addition of a flavourant may not conceal the taste or the irritating effect very well or long enough.

WO 95/20 411 describes a method of converting a medicament to a form usable for administration of the medicament to the airways or respiratory tracts of mammals. This is to bring the medicament to the location where it will do most good on people suffering from respiratory problems, such as asthma.

WO 99/6550 describes an inhalation device for providing pulmonary medicament for inhalation where the inhalation device includes a vortex generator. The vortex created through this vortex generator gives the smoker a feeling of "mouthfulness" close to what is experienced when smoking a cigarette.

GB 2 308 992 A describes a nebulizer for administering an aerosol to the lungs of patients requiring respiratory therapy, by producing a large number of small droplets and fewer large droplets in the aerosol produced by the nebulizer.

All said devices for oral administration describe means and methods for specific local delivery into the respiratory tracts, where the aim is to avoid as much as possible of the aerosol to deposit in the oral cavity.

Thus, there is a need for a delivery system, which solves the above mentioned problems associated with oral administration of substances, such as drugs and medicaments, having a bad, irritating or otherwise disagreeable taste and at the same time achieve an efficient medication, i.e. an efficient blood concentration of the substance.

SUMMARY OF THE INVENTION

The main object of the present invention is to provide means and methods for overcoming the disadvantages and solving the problems associated with the foregoing known devices for oral delivery of a substance having a bad or disagreeable taste and/or being a source of irritation.

A further object of the present invention is to provide means and methods for overcoming the above disadvantages and solving the above problems while at the same time achieving an efficient absorption of the substance.

Further objects of the invention will appear from the following description and the appending claims.

To fulfil these objects the present invention relates to an aerosol spray device for administering a substance to the oral cavity of a subject, said aerosol spray device comprising an actuator having an actuator head with a defined axis and at least one orifice the actuator head being constructed to dispense the aerosol spray containing the substance in the front of the oral cavity of the subject.

The invention also relates to an actuator being adapted to be used in such an aerosol spray device.

Furthermore, the invention refers to a method for oral administration of a substance to a subject, comprising delivering an aerosol spray containing the substance to the front of the oral cavity of the subject.

In one embodiment the invention refers to a method of assisting in the reduction of the desire of a subject to use nicotine or nicotine containing compositions, comprising delivering a nicotine containing aerosol spray to the front of the oral cavity of the subject.

By means of the means and methods provided by the present invention a bad and disagreeable taste of a drug may be reduced or substantially avoided resulting in better compliance, less irritation and other untoward effects, which in turn means more efficient therapy.

We have surprisingly found that by administering the above type of substance in the front of the oral cavity, such as below the tongue or between the lips and the teeth the experience of bad and disagreeable taste and irritation may be largely reduced or substantially eliminated at the same time as the effect of the substance is substantially maintained.

SHORT DESCRIPTION OF DRAWINGS

FIG. 1A shows a side elevation view of a first embodiment of an aerosol spray device according to the invention, FIG. 1B shows a front view of the top portion of FIG. 1A, FIG. 2A shows a side elevation view of a second embodiment of an aerosol spray device according to the invention, FIG. 2B shows a front view of the top portion of FIG. 2A, FIG. 3A shows a side view of a third embodiment of a top portion for use with an aerosol spray device according to the invention, FIG. 3B shows a front view of the top portion of FIG. 3A, FIG. 4A shows a side view of a fourth embodiment of a top portion to be used with an aerosol spray device according to the invention, and FIG. 4B shows a front view of the top portion of FIG. 4A.

DETAILED DESCRIPTION OF THE INVENTION

Definitions

The term "aerosol spray device" is intended to mean a device for atomisation, dispersion and mixing of a fluid or powdery substance for the production of an aerosol.

The term "actuator" is intended to mean a means for delivering and controlling a spray or fine mist. The actuator comprises, for this purpose, an actuator head having an orifice for generation of a desired spray or spray pattern.

The term "administration to the oral cavity" is intended to mean delivering to and absorption in the oral cavity of a subject.

The term "disagreeable taste" is intended to mean any taste, which in general is regarded as bad, nasty, or gives negative associations, such as nausea and indigestion, or is a source of irritation to the recipient.

The term "irritation" is intended to mean irritating effects such as burning, acrid or stinging effects or the like.

The Aerosol Spray Device

In order to avoid a bad or disagreeable taste and irritation from a medicine substance, such as nicotine, we have found that the spray from a spray actuator has to be delivered to the front of the oral cavity of the subject receiving the substance. This is accomplished by means of a spray device according to the invention as described below in conjunction with the drawings. The spray or spray pattern delivered deposits the sprayed liquid in the front of the oral cavity either in front of the mandibular front teeth between the lips and the teeth, just behind the teeth or under the tongue, which thereby minimises bad taste and irritation. The actuator could be constructed according to, but not limited to the appended drawings.

With reference to FIG. 1A there is shown an aerosol spray device 10. Said spray device includes a spray bottle 11 adapted to include a fluid and a top portion 17. The top portion 17 includes a cap portion 12 and an actuator 16 according to the invention. The actuator 16, having a defined axis a-a, includes a tube portion 13 and an actuator head 14 being provided with two orifices 15. A front view of the top portion 17 of said aerosol spray device 10 is shown in FIG. 1B. The actuator head 14 has the form of a plate and the two orifices 15 are placed one on each side of the actuator head 14 along the actuator head axis a-a. The fluid included in the spray bottle 11 is in this embodiment dispersed substantially perpendicular to the axis a-a of the actuator head 14, as shown in FIG. 1B.

In FIG. 2A there is shown a second embodiment of an aerosol spray device 20. In analogy with the embodiment of FIGS. 1A and B said spray device includes a spray bottle 21 and a top portion 27. The top portion 27 includes a cap portion 22 and an actuator 26 according to the invention. The actuator 26 includes a tube portion 23 and an actuator head 24 provided with two orifices 25. A front view of the top portion 27 of said aerosol spray device 20 is shown in FIG. 2B. In this embodiment the orifices 25 are placed on the top and bottom side of the actuator head 24 having the form of a plate along an axis being substantially normal to the axis a-a of the actuator head 24. The fluid included in the spray bottle 21 is also in this embodiment dispersed substantially perpendicular to the axis of the actuator head 14, as shown in FIG. 2B.

The spray devices shown in FIGS. 1A-B and 2A-B are particularly useful for administration of a spray in front of the mandibular front teeth behind the lips.

Figure 1A:
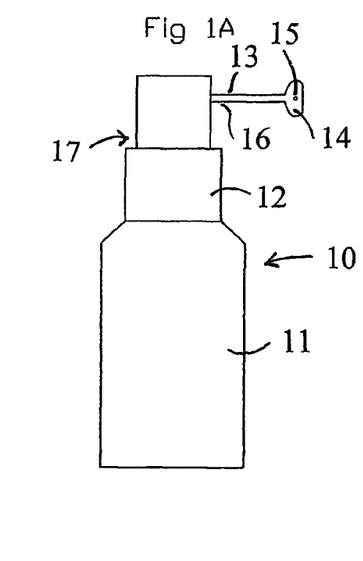
Figure 1B:
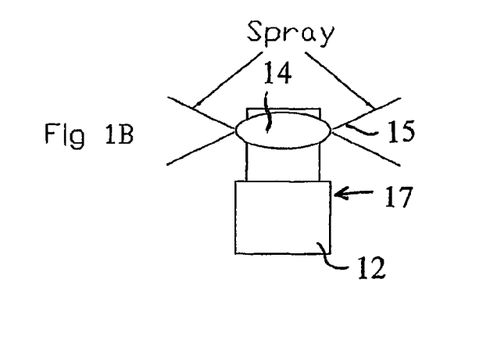
Figure 2A:
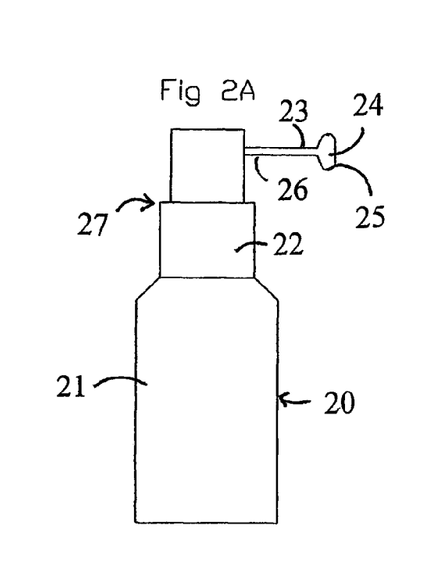
Figure 2B:
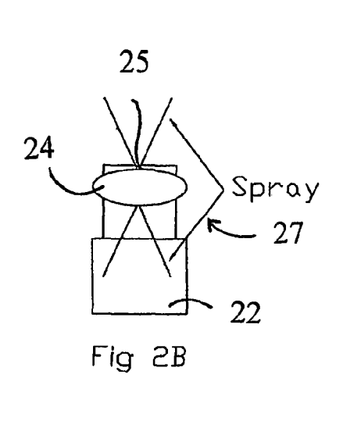
Figure 3A:
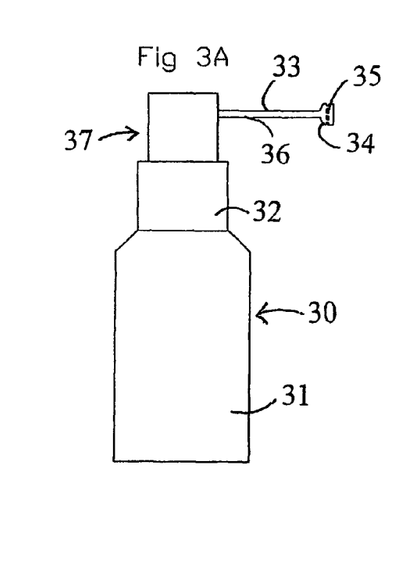
Figure 3B:
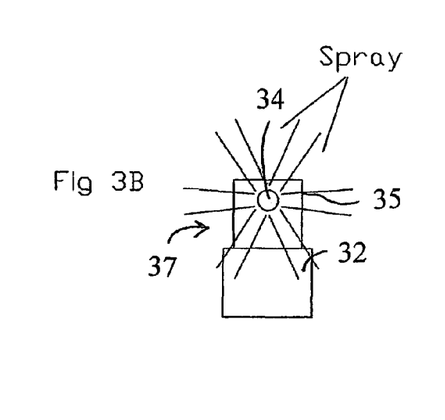

In FIG. 3A there is shown a third embodiment of an aerosol spray device 30 according to the invention. In analogy with the embodiment of FIGS. 1A-B and 2A-B respectively, said spray device includes a spray bottle 31 and a top portion 37. The top portion 37 includes a cap portion 32 and an actuator 36 according to the invention. The actuator 36 includes a tube portion 33 and an actuator head 34 provided with six orifices 35. A front view of the top portion 37 of said aerosol spray device 30 is shown in FIG. 3B. In this embodiment the orifices 35 are evenly spread round the periphery of actuator head 34. The fluid included in the spray bottle 31 is also in this embodiment dispersed substantially perpendicular to the axis of the actuator head 34.

The spray device according to FIGS. 3A-B is particularly useful for administration of a spray just behind the teeth.

Figure 4A:
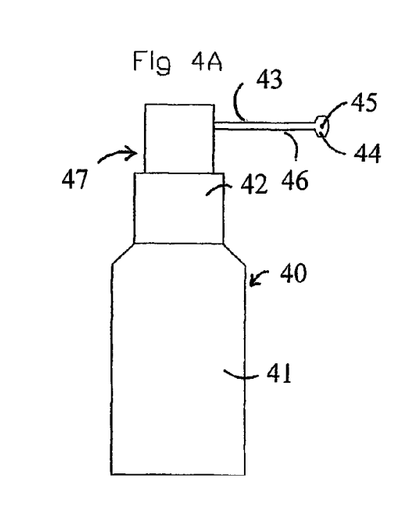
Figure 4B:
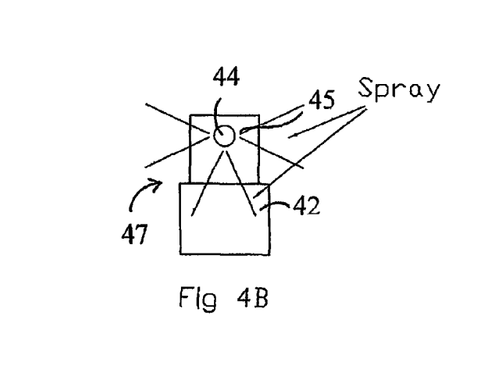

In FIG. 4A there is shown a fourth embodiment of an aerosol spray device 40 according to the invention. In analogy with the embodiment of FIGS. 1A-B, 2A-B and 3A-B, respectively, said spray device includes a spray bottle 41 and a top portion 47. The top portion 47 includes a cap portion 42 and an actuator 46 according to the invention. The actuator 46 includes a tube portion 43 and an actuator head 44 provided with three orifices 45. A front view of the top portion 47 of said aerosol spray device 40 is shown in FIG. 4B. In this embodiment the orifices 45 are placed in the lower part of the periphery of the actuator head 44. The fluid included in the spray bottle 41 in this embodiment is dispersed downwards in a half circle substantially perpendicular to the axis of the actuator head 44.

The spray device according to FIGS. 4A-B is particularly useful for sublingual administration.

The actuator according to the invention may be constructed in many different ways.

The spray actuator according to the invention comprises an actuator head having a defined axis and being provided with an orifice, where said orifice generates a spray or spray pattern directed in an angle of substantially 90±35 degrees from the actuator head axis.

The actuator may have different lengths and directions in relation to the spray bottle. The actuator head may be constructed into different forms, such as into the form of a divers mouthpiece or being provided with a flange in front of the actuator head with the aim of creating a distance between the lips and the teeth, thereby facilitate the delivering of the spray. The actuator head may also be constructed in an arched or curved form to follow the teeth and the orifices may then be distributed along part of or the whole arched or curved form.

The orifices may be of different size and shape, which will effect the spray pattern dispensed from the orifices. The actuator head may include one or more orifices. Preferable it includes many orifices, evenly distributed around the circumference of the actuator head. The sizes and the shape of holes may vary and is defined according to what is appropriate for the administration in question.

In one embodiment the actuator have a direction perpendicular to the axis of the spray bottle, as shown in the appended drawings, and the spray is directed in an angle of substantially 90 degrees to the axis a-a of the actuator head. Another embodiment may be an embodiment, where the actuator is directed along the axis of the spray bottle and the actuator head is directed substantially perpendicular to the actuator and axis of the spray bottle.

The spray bottle may be any known type, such as a pump spray or any other means for providing a spray. The spray may be provided by means of a pressurised gas.

The actuator may be made of any suitable material, such as a plastic material, or any other material well known within the art to be suitable for this type of device.

Mode of Administration

To obtain a local administration of the substance to the front of the oral cavity of a subject, the spray pattern delivering the substance is preferably directed in about 90±35 degrees to the actuator to minimize and/or exclude deposition of the substance in the back of the mouth. This will in turn reduce or substantially avoid the bad and unpleasant taste and irritating effect of a substance. A correct positioning of the device according to the invention, such as a as shown in the appended drawing, will give an administration in front of the oral cavity of a subject. Specifically the aerosol spray is administered to the front of the mandibular front teeth, i.e. in front of the teeth between the lips and the teeth, just behind the teeth or under the tongue.

Thus, in one embodiment the spray pattern delivering the substance is directed at an angle between about 55 and 125 degrees to the axis a-a of the end of the actuator nearest to the mouth.

In a further embodiment the spray pattern delivering the substance is directed at an angle between about 90 and about 125 degrees to the axis a-a of the end of the actuator nearest to the mouth; i.e. the spray is delivered upwards and obliquely backwards.

In a still further embodiment the spray pattern delivering the substance is directed at an angle of about 90 degrees to the axis a-a of the actuator; i.e. the spray is delivered substantially neither backwards nor forwards.

The examples below show that administration of an aerosol nicotine spray to the front of the oral cavity by means of an aerosol spray device adapted for such an administration reduces or substantially avoids the bad and unpleasant taste and irritating effect of a substance, while simultaneously giving substantially the same absorption and thereby effect of said substance.

Substances to be Administered

Suitable substances for distribution with the actuator according to the invention are any drug or medicament suitable for oral administration giving a bad and unpleasant taste and/or irritating effect. Examples of such substances are alkaloids, such as nicotine, nicotine salts and esters, other nicotine derivatives, lobeline, lobeline salts and esters, other lobeline derivatives; meclozine diphenhydralamine and promethazin.

Nicotine is a good example of an irritating substance with a less pleasant taste. Administering such substances via a mouth spray, vapour or aerosol is problematic. When ingested in larger doses, nicotine is a highly toxic poison that causes vomiting and nausea, headaches, stomach pains, and, in severe cases, convulsions, paralysis, and death. Even ingested in minor doses, nicotine is still an irritating, strong and bad tasting compound causing e.g. irritation in the oral cavity and respiratory tracts. In order to reduce or avoid such irritation the substance in e.g. a spray should be administered to the frontal part of the mouth. The more frontal the less irritation and bad taste.

When administering nicotine it may be in the form of the free base.

The active substance, such as nicotine or any of the substances mentioned below, may be administered together with any suitable additive known within the art, such as flavourings, preservatives and alcohol.

Administration Methods

The invention refers to a method for oral administration of a substance to a subject, comprising delivering an aerosol spray containing the substance to the front of the oral cavity of the subject.

The substance may be any substance as described under Substances to be administered above.

In one embodiment the invention refers to a method for oral administration of nicotine to a subject, comprising delivering an aerosol spray containing nicotine to the front of the oral cavity of the subject.

In a further embodiment the invention refers to a method of assisting in the reduction of the desire of a subject to use nicotine or nicotine containing compositions, comprising delivering a nicotine containing aerosol spray to the front of the oral cavity of the subject.

The nicotine containing aerosol spray may be administered to the front of the mandibular front teeth, i.e. in front of the teeth between the lips and the teeth, to the area just behind the teeth or under the tongue. The doses of nicotine to be administered are well known within the art. Typical examples are 0.5-6 mg doses of nicotine, specifically 2-4 mg doses of nicotine.

The use of nicotine or a nicotine containing composition may be the use of cigarettes, cigars, snuff, chewing tobacco and the like.

EXAMPLES

Example 1

The effect of administering 2 mg of nicotine at different sites in the mouth was studied in a study involving eight volunteer smokers. Each of 1A, 1B and 1C include all eight smokers. There was a three hours interval between the three administration conditions. The nicotine was administered in the form of a spray including in volume %:

| | |
|---|---|
| Nicotine | 1.45% |
| Alcohol | 79.71% |
| Glycerine | 14.78% |
| Flavour | 3.94% |
| Saccharine | 0.12% |

In 1A and 1B the nicotine was administered to the following sites: 1A. in front of the mandibular front teeth, 1B below the tongue. In 1C, the control group, the nicotine spray was administered in the ordinary way according to general instructions given for nicotine sprays aiming at the sides of the mouth. The degree of irritation and unpleasant taste, respectively was rated at 5 min after application using a VAS (visual analogue scale, 100 mm; 0 mm means no irritation or unpleasant taste and 100 mm means maximal irritation and unpleasant taste, respectively). Blood tests were carried out immediately before and 15 minutes after the administration of the nicotine dose and the nicotine plasma levels were determined as the Δ plasma nicotine value.

The device used was a standard Nussbaum & Guhl pump.
Results:

| Administration | Irritation (mm) | SD* | Unpleasant taste (mm) | SD* | Δ plasma nicotine ng/ml |
|---|---|---|---|---|---|
| 1A | 63 | 14.6 | 61 | 10.4 | 5.5 |
| 1B | 59 | 12.9 | 63 | 9.8 | 5.4 |
| 1C | 82 | 13.1 | 71 | 12.6 | 4.3 |

*SD = standard deviation

As to the degree of irritation 1C was significantly higher than both 1A and 1B ($p<0.01$, two tailed test). As to the degree of unpleasant taste 1C was significantly higher than 1A ($p<0.01$, two tailed test) and 1C was also higher than 1B ($p<0.05$, two tailed test).

Example 1 shows that an administration of a nicotine spray in the front of the oral cavity gives less irritation and unpleasant taste compared to ordinary administration in the whole oral cavity. The absorption of nicotine, i.e. the effect of the nicotine is however not reduced.

Example 2

A second experiment was performed using ten volunteer smokers. Each of 2A, 2B and 2C included all ten smokers. As in example 1 there was a three hours interval between the administration conditions. In 2A a 2 mg nicotine mouth spray using a standard Nussbaum & Guhl pump was used and the dose was administered in the same ordinary way according to general instructions given for nicotine sprays as in 1C above. In 2B 2 mg and in 2C 4 mg of nicotine was given by means of the device shown in FIG. 1A. The doses 2A and 2B were administered in front of the mandibular front teeth.

Said nicotine spray had the same composition as the spray in example 1 and irritation, unpleasant taste as well as Δ plasma nicotine were rated and measured in the same way as in example 1.
Results:

| Administration | Irritation (mm) | SD* | Unpleasant taste (mm) | SD* | Δ plasma nicotine ng/ml |
|---|---|---|---|---|---|
| 2A | 64 | 10.8 | 62 | 11.3 | 5.7 |
| 2B | 41 | 9.0 | 43 | 8.9 | 5.5 |
| 2C | 65 | 11.0 | 61 | 13.0 | 7.2 |

*SD = standard deviation

As to the degree of both irritation and unpleasant taste 2A was significantly higher than 2B ($p<0.01$, two tailed test) and the values of 2C was also significantly higher than 2B ($p<0.01$, two tailed test).

When comparing 2A and 2B this example 2 also shows that administration of the nicotine to the front of the oral cavity (2B), here the front of the mandibular front teeth, gives much less irritation and unpleasant taste compared to ordinary administration in the whole oral cavity (2A), still having substantially the same effect. 2C shows that a dose of 4 mg (double dose) administered in the front of the mandibular front teeth does not give more irritation and unpleasant taste than half the dose (2 mg) administered in the ordinary way into the whole oral cavity.

Example 3

The experiment described in Example 2 was repeated using ten volunteer smokers. In 3A a 2 mg nicotine mouth spray using a standard Nussbaum & Guhl pump was used and in 3B 2 mg and 3C 4 mg of nicotine was given by means of the aerosol spray device shown in FIG. 1A. All nicotine doses (3A-3C) were administered below the tongue.

Results:

| Administration | Irritation (mm) | SD* | Unpleasant taste (mm) | SD* | Δ plasma nicotine ng/ml |
|---|---|---|---|---|---|
| 3A | 69 | 13.3 | 62 | 12.8 | 6.9 |
| 3B | 46 | 9.8 | 44 | 10.4 | 7.7 |
| 3C | 71 | 14.5 | 63 | 13.8 | 10.1 |

*SD = standard deviation

As to the degree of both irritation and unpleasant taste 3A was significantly higher than 3B ($p<0.01$, two tailed test) and the values of 3C was also significantly higher than 3B ($p<0.01$, two tailed test).

Example 3 shows that administration of the nicotine spray by means of a device, such as a device according to the invention, adapted for administration of the spray into the very front of the oral cavity reduces both irritation and unpleasant taste, but not the absorption of nicotine.

The invention claimed is:

1. An aerosol spray device, comprising a spray bottle containing a substance and having an actuator engaged therewith and configured for releasing the substance from the spray bottle, the actuator extending from the spray bottle along a first axis, the actuator further including a tubular member extending therefrom along a longitudinal axis and defining a first channel extending along the longitudinal axis, the longitudinal axis being non-parallel to the first axis, and engaged with a dispensing head distally to the actuator, the dispensing head defining an axis parallel with the longitudinal axis of the tubular member and having a larger dimension transverse to the dispensing head axis than the tubular member transverse to the longitudinal axis, the dispensing head defining at least one orifice in communication with the first channel and configured to dispense therethrough an aerosol spray containing the substance released from the spray bottle, via the actuator and the first channel upon actuation of the actuator, at an angle of substantially 90±35 degrees with respect to the dispensing head axis, the dispensing head thereby being adapted to administer the substance to an oral cavity of a subject by directing the aerosol spray directly to an area in the front of the mandibular teeth of the subject, an area behind the teeth of the subject, or an area under the tongue of the subject.

2. The device according to claim 1, wherein the substance has a disagreeable taste and/or is a source of irritation.

3. The device according to claim 1, wherein the substance is selected from the group consisting of alkaloids, including nicotine, nicotine derivatives, nicotine salts, lobeline, lobeline derivatives and lobeline salts; meclozine diphenhydralamine and promethazin.

4. The device according to claim 1, wherein the substance is nicotine.

5. The device according to claim 4, wherein the nicotine is in the form of a free base.

6. The device according to claim 1, wherein the orifices are evenly spread around a periphery of the dispensing head.

7. The device according to claim 1, wherein the orifices are disposed in a lower part of the dispensing head.

8. A spray device including an actuator adapted to engage a source of a substance, the actuator being configured for releasing the substance from the source and extending from the source along a first axis, the actuator further having a tubular member extending therefrom along a longitudinal axis and defining a first channel extending along the longitudinal axis, the longitudinal axis being non-parallel to the first axis, and engaged with a dispensing head distally to the actuator, the dispensing head extending along the longitudinal axis and having a larger dimension than the tubular member transverse to the longitudinal axis, the dispensing head defining at least one orifice in communication with the first channel and adapted to dispense therethrough an aerosol spray containing the substance released from the source via the actuator and the first channel upon actuation of the actuator, the at least one orifice being configured with respect to the dispensing head such that the aerosol spray is dispensed at an angle of substantially 90±35 degrees with respect to the longitudinal axis of the tubular member, the dispensing head thereby being adapted to administer the aerosol spray containing the substance directly to an area in front of the mandibular teeth of a subject, an area just behind the teeth of the subject, or an area under the tongue of the subject.

9. A method for oral administration of a substance to a subject, comprising delivering an aerosol spray containing the substance to the front of the oral cavity of the subject, via a spray device including an actuator engaged with a source of the substance and extending from the source along a first axis, the actuator being further configured for releasing the substance from the source, the actuator having a tubular member extending therefrom along a longitudinal axis and defining a first channel extending along the longitudinal axis, the longitudinal axis being non-parallel to the first axis, and engaged with a dispensing head distally to the actuator, the dispensing head extending along the longitudinal axis and having a larger dimension than the tubular member transverse to the longitudinal axis, and the dispensing head defining at least one orifice in communication with the first channel, by directing the aerosol spray containing the substance released from the source, through the actuator and the first channel defined by the interposed tubular member, and through the at least one orifice upon actuation of the actuator such that the aerosol spray is dispensed at an angle of substantially 90±35 degrees with respect to the longitudinal axis of the tubular member to the front of the oral cavity of the subject during the delivery to substantially avoid deposition of the substance in the back of the mouth.

10. The method according to claim 9, wherein the front of the oral cavity is an area in front of the mandibular teeth of the subject, an area just behind the teeth of the subject, or an area under the tongue of the subject.

11. The method according to claim 9, wherein the substance has a disagreeable taste and/or is a source of irritation.

12. The method according to claim 11, wherein the substance is selected from the group consisting of alkaloids, including nicotine, nicotine derivatives, nicotine salts, lobeline, lobeline derivatives and lobeline salts; meclozine diphenhydralamine and promethazin.

13. The method according to claim 11, wherein the substance is nicotine.

14. The method according to claim 13, wherein the nicotine is in the form of a free base.

15. A method for assisting in the reduction of the desire of a subject to use nicotine or nicotine containing compositions, comprising delivering an aerosol spray including a nicotine containing substance directly to an area in the front of the oral cavity of a subject from a spray device including an actuator engaged with a source of the nicotine containing substance and extending from the source along a first axis, the actuator being further configured for releasing the nicotine containing substance from the source, the actuator having a tubular member extending therefrom along a longitudinal axis and defining a first channel extending along the longitudinal axis, the longitudinal axis being non-parallel to the first axis, and engaged with a dispensing head distally to the actuator, the dispensing head extending along the longitudinal axis and having a larger dimension than the tubular member transverse to the longitudinal axis, and the dispensing head defining at least one orifice in communication with the first channel, by directing the aerosol spray including the nicotine containing substance released from the source, through the actuator and the first channel defined by the interposed tubular member, and through the at least one orifice upon actuation of the actuator such that the aerosol spray including the nicotine containing substance is dispensed at an angle of substantially 90±35 degrees with respect to the longitudinal axis of the tubular member to the front of the oral cavity of the subject during the delivery to substantially avoid deposition of the substance in the back of the mouth.

16. The method according to claim 15, wherein the front of the oral cavity is an area in front of the mandibular teeth of the subject, an area just behind the teeth of the subject, or an area under the tongue of the subject.

17. The method according to claim 15, wherein the nicotine containing aerosol spray contains nicotine in the form of a free base.

* * * * *